(12) United States Patent
McNenny

(10) Patent No.: US 7,163,515 B2
(45) Date of Patent: Jan. 16, 2007

(54) PROJECTILE BLOOD COLLECTION DEVICE

(76) Inventor: James H. McNenny, 2727 York Dr., Stow, OH (US) 44224

( * ) Notice: Subject to any disclaimer, the term of this patent is extended or adjusted under 35 U.S.C. 154(b) by 295 days.

(21) Appl. No.: 10/651,417

(22) Filed: Aug. 30, 2003

(65) Prior Publication Data

US 2004/0133126 A1   Jul. 8, 2004

Related U.S. Application Data

(60) Provisional application No. 60/407,575, filed on Sep. 3, 2002.

(51) Int. Cl.
  *A61B 5/00*  (2006.01)
  *A61B 19/00* (2006.01)
  *A61B 17/14* (2006.01)
  *A61M 37/00* (2006.01)
  *A61M 1/00*  (2006.01)
  *A61M 5/32*  (2006.01)

(52) U.S. Cl. .................... 600/573; 600/578; 604/6.15; 604/317; 604/411; 606/167; 606/181

(58) Field of Classification Search ............... 600/573, 600/578, 583; 606/182, 181, 167; 604/3.15, 604/317, 411, 6.15
See application file for complete search history.

(56) References Cited

U.S. PATENT DOCUMENTS

| 4,517,978 A * | 5/1985 | Levin et al. ............... 606/182 |
| 5,324,303 A * | 6/1994 | Strong et al. .............. 606/181 |
| 5,368,047 A * | 11/1994 | Suzuki et al. .............. 600/578 |
| 6,210,420 B1 * | 4/2001 | Mauze et al. .............. 606/182 |
| 6,332,871 B1 * | 12/2001 | Douglas et al. ............ 600/583 |
| 2002/0111565 A1 * | 8/2002 | Roe et al. ................. 600/578 |

* cited by examiner

*Primary Examiner*—Max F. Hindenburg
*Assistant Examiner*—Jeffrey G Hoekstra

(57) ABSTRACT

This disclosure describes a device for obtaining a blood sample from an intruder at a crime scene to be later analyzed for DNA. A projectile containing a blood-extracting needle for penetrating the skin of said intruder is mounted through a protective chamber and connected to a blood reservoir in the chamber interior. A vacuum is held in both the reservoir and the chamber. The chamber vacuum is released by forward movement of the chamber as it slides within a casing following further penetration of the needle. The vacuum release acts to reduce the ambient pressure within the forward portion of the casing, thus assisting in propelling the needle into the intruder. As the needle reaches maximum extension, a loaded spring within the casing is released, propelling the needle and reservoir away from the intruder.

3 Claims, 2 Drawing Sheets

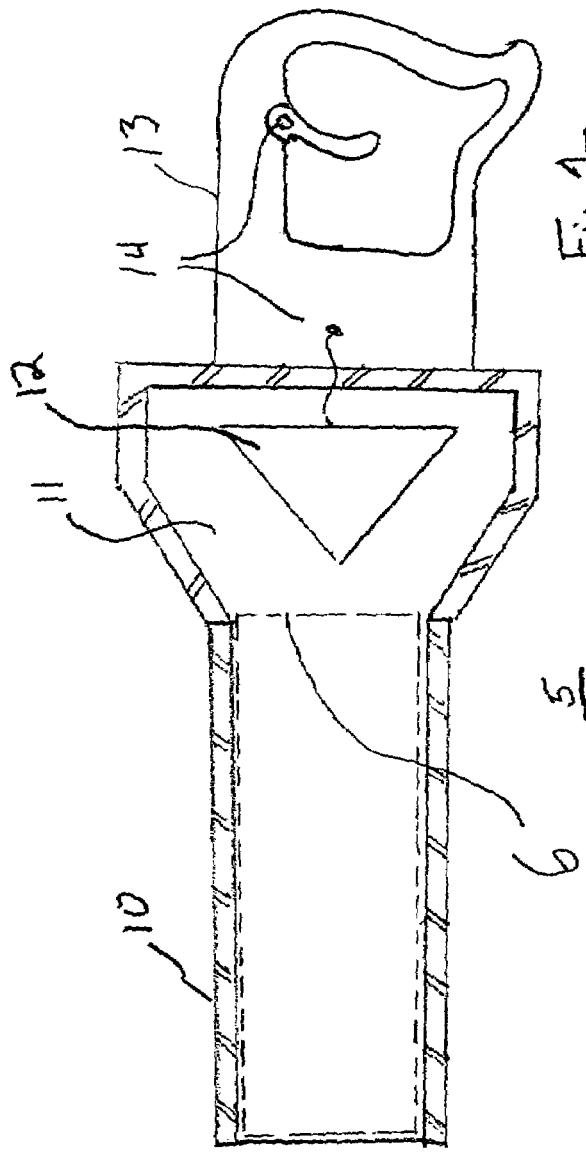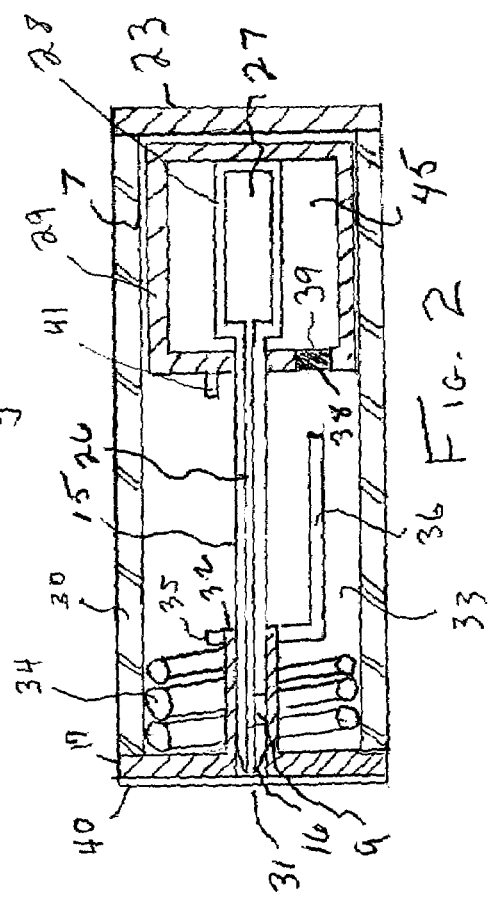

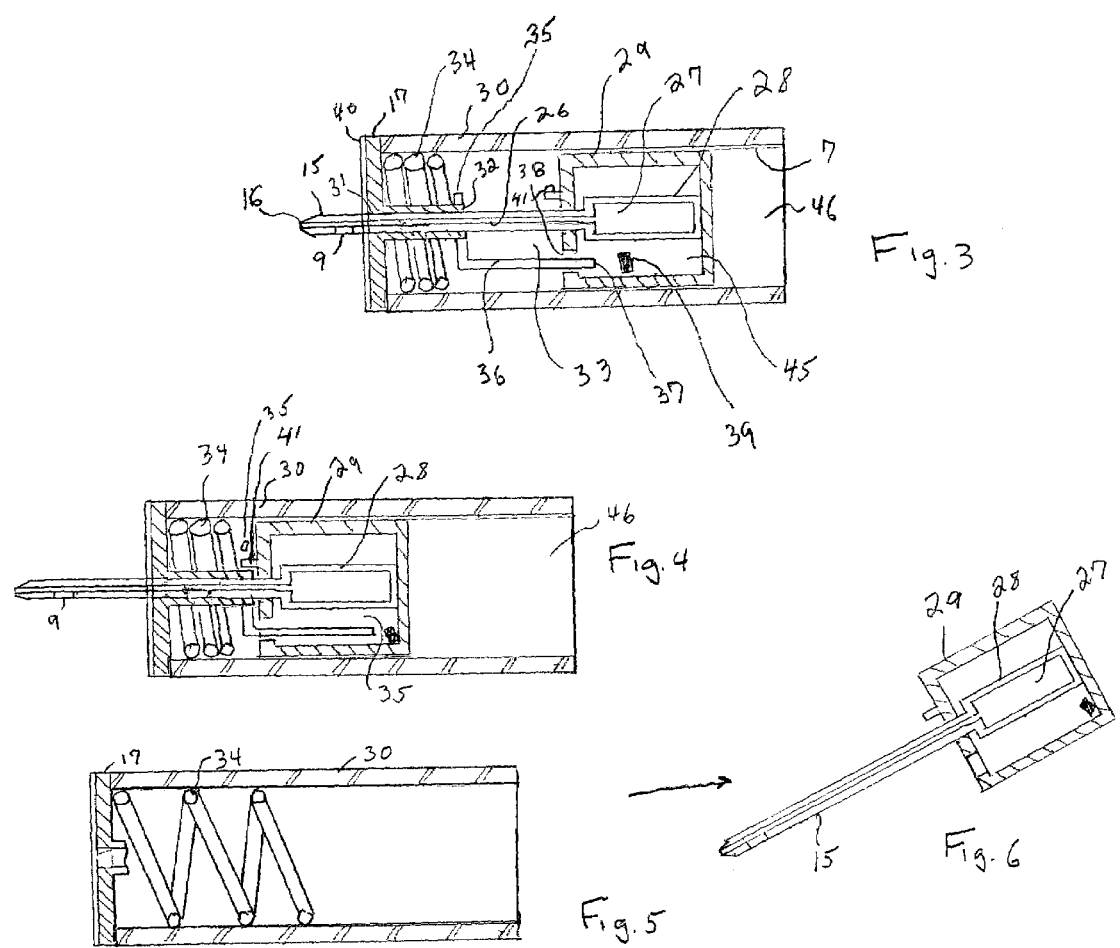

PROJECTILE BLOOD COLLECTION DEVICE

REFERENCE TO RELATED PROVISIONAL PATENT APPLICATION

This application contains subject matter disclosed in Provisional Patent Application No. 60/407,575 filed Sep. 3, 2002 in the name of the Applicant herein.

FIELD OF THE INVENTION

This invention relates to crime deterrence; and in particular to identifying a perpetrator in the commission of crimes such as burglary, robbery, breaking and entering, and other criminality involving the unauthorized entering of private space and property.

BACKGROUND OF THE INVENTION

Many conventional technologies are routinely practiced by law enforcement agencies to identify a perpetrator, including fingerprinting, video surveillance, and foot printing. Each also is a deterrent to the commission of crime since criminals know that their widespread use makes it more likely that a perpetrator can be identified and prosecuted.

These methodologies have their limitations, however, because each can be defeated or at least countered by the criminal. Use of gloves or a facemask, for example, defeats identification by fingerprinting or video surveillance.

Defenses against crimes of intrusion by potential victims routinely include handguns, mace, stunning devices and the like, which have in common the requirement that the victim must brandish the deterring weapon in close proximity to the criminal intruder. Besides being daunting and dangerous to the victim acting in self-defense, confronting seasoned criminals does not necessarily result in identification. Confronted by weapons, it is all too usual for the criminal to "get the drop" on the victim, or to withdraw from the crime scene. In either case the criminal is not likely to be identified.

SUMMARY OF THE INVENTION

This invention is a novel approach to deterring crimes of intrusion, by making it more likely that the perpetrator will be identified. Instead of attempting to deter a criminal with methodologies that can be circumvented or fairly readily overcome, such as in the case of guns or video surveillance, this invention is a mechanism for obtaining a blood sample from the intruder to be later analyzed for DNA.

The invention brings the elements of surprise and speed to the extraction of a blood sample; and thereafter, the invention effectively withdraws the sample from the point of contact by a random ejecting of the blood sample reservoir outside the cognizance of the criminal at the crime scene.

In a particular embodiment, the invention comprises a self-contained device featuring a skin and clothing-penetrating needle and reservoir assembly, which travels with an extracting and disbursing mechanism. A conventional means of launching the device is provided. Blood extracting is performed by a vacuum chamber connected to the needle interior. The needle assembly mounts onto an exterior wall of a protective chamber and is connected to a blood reservoir in the chamber interior. The chamber and needle ride in a hollow cylindrical casing that contains an eject spring. The components are launched at the intruder, either through aiming by a human or by automated means not involving the human element. The impact on the intruder is non-lethal in concept: the needle and chamber assembly slide in the casing by their flight momentum; and the needle emerges from the casing to commence penetration of the criminal's skin. Insertion is only deep enough to encounter a blood supply. Penetration of the skin is assisted by drawing down the atmospheric pressure in front of the advancing needle, by connecting it to the vacuum of the chamber containing the reservoir. Blood is drawn into the chamber's reservoir even as the device continues to complete its connection to the intruder. At a point during the reservoir filling, the still-traveling chamber trips a spring actuator, which causes the spring to discharge against the needle, and chamber assembly. The action propels the blood sample away from the intruder a distance of some feet or yards.

Depending on the surrounds at the scene, the DNA-containing chamber will be irretrievable to the criminal because he does not know where to look for it, what to look for, or even whether to look for something. Thus, in addition to possibly being thwarted in the commission of the crime, it is likely that the intruder will leave behind at the crime scene a sample of blood to be located later by the police.

DESCRIPTION OF THE DRAWINGS

FIG. 1 is a schematic side diagram of a version of the invention, which is hand-held;

FIG. 2 is a cross-sectional side view of the projectile assembly in an at-rest position;

FIG. 3 is a cross-sectional side view of the projectile assembly with the interior parts shown in motion just after contact with a body;

FIG. 4 is a is a cross-sectional side view of the projectile assembly with the needle and associated chambers at their fullest extension;

FIG. 5 is a cross-section of the projectile assembly ejecting away from the intruder following actuation of an eject spring; and FIG. 6 shows a cross-section of the ejected needle, blood reservoir and chamber assembly in flight.

DETAILED DESCCRIPTION OF AN ILLUSTRATIVE EMBODIMENT

FIG. 1 shows the general working of the invention, embodied in an overall device designated 5 which may be a hand-held item or alternatively a stand, wall, or ceiling-mounted device. Device 5 consists of a barrel 10, a detonation chamber 11, in which is housed a propellant 12, a handle or grip 13 and a triggering mechanism 14 connected to actuate propellant 12. It is understood that propellant 12 may be conventional explosive powder such as used in shot gun ammunition; or a gas cartridge. The chosen propellant is activated in a manner appropriate to it by selecting of a trigger device 14 of which many are well known in the art.

Housed in barrel 10 is needle projectile assembly 6 shown only in dotted line outline in FIG. 1. Referring now to FIG. 2, needle projectile assembly 6 consists of a needle 15 with an inner passage 26 that hydraulically connects to a reservoir 27 formed in the hollow interior of a cylindrical chamber 28. Chamber 28 in turn is fixedly mounted within an outer chamber 29. Chamber 29 slidbly moves in piston-like fashion along the cylindrical interior wall 7 of a cylindrical casing 30.

FIG. 2 shown the components of the needle projectile assembly 6 in their at-rest position, that is, as situated before firing from barrel 10. Chamber 29 and needle 15 with its associated chamber 28 and reservoir 26 are positioned to the rear of casing 30 adjacent to a solid cap plate 23 which is fastened to the ends of casing 30 by, for example, an adhesive (not shown). Solidly fastened to the front end of casing 30 as by welding, is a facing 17 having a center circular opening 31 formed with substantially the same diameter as needle 15. The point 16 of needle 15 protrudes slightly from opening 31 when in the at-rest position. Facing 17 includes a hollow collar 32 extending into the space 33 within casing 30 that is forward of chamber 29. An entry orifice 9 in needle 15 connecting to passage 26 is hermetically sealed by the inside cylindrical surface of collar 32 to safeguard against any contaminants lodging in the passage 26 or reservoir 17. Collar 32 slidably mounts needle 15 in a way that allows needle 15 to travel forward and back during its operation, as will be explained below.

A coil spring 34 is butted up against the interior surface of facing 17 and is held in compression by a pin 35 affixed to the end of collar 32. Also mounted from collar 32 is an elongate pushrod 36, the end 37 of which is oriented toward an entry hole 38 in chamber 29. A snug-fitting elastic plug 39 is frictionally lodged in hole 38, so that an initial high vacuum can be imparted to the interior void 45 of chamber 29.

FIG. 3 shows the needle projectile assembly 6 shortly following its launch from barrel 10, at a point when the assembly has encountered the body and clothes of an intruder (not shown). During flight, plate 23 has separated from its adhesive mount on the end of casing 30, thus opening the end of casing 30 for the exiting of needle 15 and its connected chambers 26 and 28 later. The impact stops casing 30 and the components connected to it including collar 32, spring 34 and rod 36. The momentum of needle 15 and the connected chamber 26 and chamber 28, however, cause these components to continue traveling into the space 33. During this travel, needle 15 emerges through a protective membrane 40 that covers the outside surface of facing 17; and its point 16 commences its penetration of the intruder's clothes and skin. The interval between the needle 15 and its blood-receiving orifice 9 from membrane 40 and its penetration into the skin of the intruder, may be controlled to within milliseconds. Blood drawing commences even before chamber 29 has completed its forward travel.

Substantially concurrent with the emergence of needle 15 from membrane 40, rod 36 impacts and dislodges plug 39 in the front wall of chamber 29. With the plug 39 dislodged, the vacuum within chamber 29 draws air at atmospheric pressure from space 33, thus greatly reducing air pressure in space 33. This pressure differential between space 33 and the space 46 to the rear of chamber 29, further drives needle 15 into the skin and body of the intruder.

FIG. 4 shows the relative positions of the casing 30 and the needle 15 when the needle-chamber assembly 15–28 reaches the spring 34. Pin 35, which normally holds spring 34 in compression, is sheared off by the forward travel of shear pin 41 formed in the face of chamber 29. As shown in FIG. 5, spring 34 is now released from its compression, and expands away from the interior surface of facing 17. Needle 15, chamber 29 and chamber 28 with its acquired sample of blood in reservoir 27 are propelled outwardly as illustrated in FIG. 6, away from the intruder.

The entire physical encounter of the described device with the intruder consumes from 1 to 2 seconds. So instantaneous is the experience that it is highly probable the intruder literally will not suspect, much less know what hit him, The blood sample is removed several feet or yards from the intruder. Its sturdy reservoir construction of the needle 15, chamber 29 and chamber 28 assembly makes it difficult to compromise without suitable tools, even if the intruder can locate it and recognize it for what it is. Police at the scene will later retrieve the assembly and analyze the blood for DNA; which when linked with the intruder will establish the element of presence at the crime scene.

Although the preceding illustrative embodiment is of a hand-held version of the invention, it is apparent that the device with routine exercise of skills in the art can be mounted on a stand, or advantageously, on a video surveillance camera

The invention claimed is:

1. A blood-collecting apparatus for obtrusively obtaining a blood sample from an intruder at a crime scene to be later analyzed for DNA, comprising:
    a blood-extracting needle for penetrating the skin of said intruder;
    a blood-collecting reservoir connected in fluid communication to said blood-extracting needle for receiving said blood sample, wherein said connected blood-extracting needle and blood-collecting reservoir form a needle-reservoir assembly;
    a first chamber, including a means for mounting said needle-reservoir assembly on said first chamber and a means for holding an initial vacuum in said first chamber;
    a cylindrical casing defining a cylindrical interior and a facing at a distal first end of said cylindrical casing having a center hole for receiving said needle-reservoir assembly, wherein said first chamber is slidably mounted in said cylindrical interior;
    a means for propelling said needle-reservoir assembly into contact with said intruder;
    a means responsive to said contact for distally advancing said blood-extracting needle through said center hole, thus promoting insertion of said needle-reservoir assembly into said intruder; and
    a coil spring positioned adjacent the interior side of said facing, including a means for retaining and securing said coil spring in a normally biased mode, and configured to extract and eject said needle-reservoir assembly a substantial distance proximally from said intruder in response to a maximum penetration.

2. The blood-collecting apparatus of claim 1, further comprising:
    an extension collar comprising an elongate proximally-extending rod and attached to said facing for slidably receiving said blood-extracting needle;
    wherein said means for holding an initial vacuum in said first chamber comprises a proximally disposed entrance to said interior of said first chamber;
    wherein a plug is inserted in said entrance; and
    wherein said rod is configured to punch out said plug in response to said contact and to release said vacuum to reduce pressure in the space occupied by said coil spring and said collar.

3. The blood-collecting apparatus of claim 2, further comprising: a distal extension disposed on the exterior of said first chamber and aligned with said means for retaining and securing said coil spring to shear said retaining means for releasing said spring and ejecting said first chamber said needle-reservoir assembly from said casing.

* * * * *